(12) United States Patent
DeLuca et al.

(10) Patent No.: US 7,115,594 B2
(45) Date of Patent: Oct. 3, 2006

(54) USE OF 2-METHYLENE-19-NOR-20(S)-1α,25-DIHYDROXYVITAMIN D$_3$ TO INCREASE BONE STRENGTH

(75) Inventors: Hector F. DeLuca, Deerfield, WI (US); Connie M. Smith, Blue Mounds, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 117 days.

(21) Appl. No.: 10/673,629

(22) Filed: Sep. 29, 2003

(65) Prior Publication Data

US 2004/0068129 A1    Apr. 8, 2004

Related U.S. Application Data

(62) Division of application No. 09/616,164, filed on Jul. 14, 2000, now abandoned.

(51) Int. Cl.
*A61K 31/59* (2006.01)

(52) U.S. Cl. ..................................... 514/167
(58) Field of Classification Search ................. 514/167
See application file for complete search history.

(56) References Cited

U.S. PATENT DOCUMENTS 5,587,497 A    12/1996    DeLuca et al.
5,843,928 A *  12/1998    Deluca et al. ............... 514/167

OTHER PUBLICATIONS

The Merck Manual, Sixteenth Edition, 1992, p. 1357.
Boris et al, "Relative Activities of Some Metabolites and Analogs of Cholecalciferol in Stimulation of Tibia Ash Weight in Chicks Otherwise Deprived of Vitamin D," Vitamin D Metabolites, Analogs and Bone Ash, 1976, pp. 194-198.
Hedlund et al, "Increased Incidence of Hip Fracture in Osteoporotic Women Treated with Sodium Fluoride," Journal of Bone and Mineral Research, vol. 4, No. 2, 1989, pp. 223-225.
Holick et al, Harrison's Principle of Internal Medicine, 13th Ed. 1994, pp. 2137-2151.
Jensen et al, "Treatment of Post Menopausal Osteoporosis, A Controlled Therapeutic Trial Comparing Oestrogen/Gestagen, 1.25-Dihydroxy-Vitamin D-3 and Calcium," Clinical Endocrinology, 16, 1982, pp. 515-524.
Meunier, "Evidence-Based Medicine and Osteoporosis: A Comparison of Fracture Risk Reduction Data from Osteoporosis Randomised Clinical Trials," IJCP, vol. 53, No. 2, Mar. 1999.
Nordin et al, "The Metabolic Basis of Osteoporosis," Osteoporosis: Physiological Basis, Assessment, and Treatment, Elsevier Science Publishing Co., Inc., 1990, pp. 23-36.
Ott et al, "Calcitriol Treatment is not Effective in Postmenopausal Osteoporosis," Annals of Internal Medicine, vol. 110, No. 4, Feb. 15, 1989, pp. 267-274.

(Continued)

*Primary Examiner*—San-Ming Hui
(74) *Attorney, Agent, or Firm*—Andrus, Sceales, Starke & Sawall, LLP

(57) ABSTRACT

This invention provides pharmaceutical uses for 2-methylene-19-nor-20(S)-1α,25-dihydroxyvitamin D$_3$. This compound is characterized by high bone calcium mobilization activity demonstrating preferential activity on bone. This results in a novel therapeutic agent for the treatment of diseases where bone formation is desired, particularly osteoporosis. This compound also exhibits pronounced activity in arresting the proliferation of undifferentiated cells and inducing their differentiation to the monocyte thus evidencing use as an anti-cancer agent and for the treatment of skin diseases such as psoriasis. This compound also increases both breaking strength and crushing strength of bones evidencing use in conjunction with bone replacement surgery such as hip and knee replacements.

10 Claims, 7 Drawing Sheets

OTHER PUBLICATIONS

Peck, "The Pathogenesis of Postmenopausal Osteoporosis," Osteoporosis: Physiological Basis, Assessment, and Treatment, Elsevier Science Publishing Co., Inc., 1990, pp. 3-6.

Riggs et al, "Bone Turnover Matters: The Raloxifene Treatment Paradox of Dramatic Decreases in Vertebral Fractures without Commensurate Increases in Bone Density,"Journal of Bone and Mineral Research, vol. 17, No. 1, 2002, pp. 11-13.

Riggs et al, "Causes of Age-Related Bone Loss and Fractures," Osteoporosis: Physiological Basis, Assessment, and Treatment, 1990, pp. 7-16.

Christensen, Abstract PMID: 6795047, "Effect of 1,25-Dihydroxy-Vitamin D3 in Itself or Combined with Hormone Treatment in Prevent Postmenopausal Osteoporosis," Eur. J. Clin. Invest., Aug. 11, 1981, vol. 11, No. 4.

Klein, "Nutritional Rickets and Osteomalacia," Primer on the Metabolic Bone Diseases and Disorders of Mineral Metabolism, 1996, pp. 301-305.

Kleerekoper, "Treatment of Osteoporosis with Sodium Fluoride Alternating with Calcium and Vitamin D," Osteoporosis: Recent Advances in Pathogenesis and Treatment, 1981, pp. 441-448.

Sarkar, "Relationships Between Bone Mineral Desnity and Incident Vertebral Fracture Risk with Raloxifene Therapy," Journal of Bone and Mineral Research, vol. 17, No. 1, 2002, pp. 1-10.

Cummings et al, "Improvement in Spine Bone Desity and Reduction in Risk of Vertebral Fractures During Treatment with Antiresorptive Drugs," The American Journal of Medicine, vol. 112, 2002, pp. 281-289.

Sudhaker Rao et al, "Metabolic Bone Disease in Gastrointestinal Hepatobiliary, and Pancreatic Disorders," Primer on the Metabolic Bone Diseases and Disorders of Mineral Metabolism, 1996, pp. 306-311.

Watts et al, "Intermittent Cyclical Etidronate Treatment of Postmenopausal Osteoporosis," The New England Journal of Medicine, vol. 323, No. 2, Jul. 12, 1990, pp. 73-79.

Harris, "Four-Year Study of Intermittent Cyclic Etidronate Treatment of Postmenopausal Osteoporosis: Three Years of Blinded Therapy Followed by One Year of Open Therapy," The American Journal of Medicine, vol. 95, Dec. 1993, pp. 557-567.

* cited by examiner

USE OF 2-METHYLENE-19-NOR-20(S)-1α,25-DIHYDROXYVITAMIN $D_3$ TO INCREASE BONE STRENGTH

CROSS-REFERENCE TO RELATED APPLICATIONS

This application is a divisional of U.S. patent application Ser. No. 09/616,164 filed Jul. 14, 2000 now abandoned.

BACKGROUND OF THE INVENTION

This invention relates to vitamin D compounds, and more particularly to pharmaceutical uses for 2-methylene-19-nor-20(S)-1α,25-dihydroxyvitamin $D_3$.

The natural hormone, 1α,25-dihydroxyvitamin $D_3$ and its analog in ergocalciferol series, i.e. 1α,25-dihydroxyvitamin $D_2$ are known to be highly potent regulators of calcium homeostasis in animals and humans, and more recently their activity in cellular differentiation has been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

Recently, a new class of vitamin D analogs has been discovered, i.e. the so called 19-nor-vitamin D compounds, which are characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Left. 31,1823 (1990); Perlman et al., Tetrahedron Left. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163,1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Recently, 2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, an analog which is characterized by the presence of a methylene substituent at the carbon 2 (C-2) has been synthesized and tested. Of particular interest is the analog which is characterized by the unnatural configuration of the methyl group at carbon 20 (C-20), i.e. 2-methylene-19-nor-20(S)-1α,25-dihydroxyvitamin $D_3$. This vitamin D analog seemed an interesting target because the relatively small methylene group at C-2 should not interfere with the vitamin D receptor. Moreover, molecular mechanics studies performed on the model 1α-hydroxy-2-methylene-19-nor-vitamins indicate that such molecular modification does not change substantially the conformation of the cyclohexanediol ring A. However, introduction of the 2-methylene group into 19-nor-vitamin D carbon skeleton changes the character of its 1α- and 3β- A-ring hydroxyls. Both hydroxyls are allylic to the exocyclic methylene group similar to the 1α-hydroxyl group (crucial for biological activity) in the molecule of the natural hormone, 1α,25-$(OH)_2D_3$.

SUMMARY OF THE INVENTION

The present invention is directed toward 2-methylene-19-nor-20(S)-1,25-dihydroxyvitamin $D_3$, its biological activity, and various pharmaceutical uses for this compound.

Structurally this 19-nor analog is characterized by the general formula I shown below:

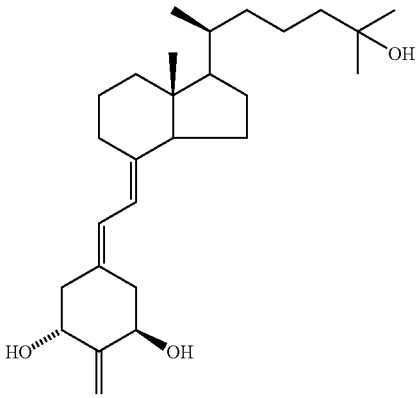

The solid wedge-shaped line to the methyl substituent at C-20 indicates that carbon 20 has the S configuration.

The above compound exhibits a desired, and highly advantageous, pattern of biological activity. This compound is characterized by intestinal calcium transport activity, similar to that of 1α,25-dihydroxyvitamin $D_3$, but exhibiting very high activity, as compared to 1α,25-dihydroxyvitamin $D_3$, in its ability to mobilize calcium from bone. Hence, this compound is highly specific in its calcemic activity. Its preferential activity on mobilizing calcium from bone allows the in vivo administration of this compound for the treatment of metabolic bone diseases where bone loss is a major concern. Because of its preferential activity on bone, this compound would be a preferred therapeutic agent for the treatment of diseases where bone formation is desired, such as osteoporosis, especially low bone turnover osteoporosis, steroid induced osteoporosis, senile osteoporosis or postmenopausal osteoporosis, as well as osteomalacia and renal osteodystrophy. The treatment may be transdermal, oral or parenteral. The compound may be present in a composition in an amount from about 0.1 μg/gm to about 50 μg/gm of the composition, and may be administered in dosages of from about 0.1 μg/day to about 10 μg/day.

The compound of the invention is also especially suited for treatment and prophylaxis of human disorders which are characterized by an imbalance in the immune system, e.g. in autoimmune diseases, including multiple sclerosis, diabetes mellitus, host versus graft reaction, and rejection of transplants; and additionally for the treatment of inflammatory diseases, such as rheumatoid arthritis and asthma, as well as the improvement of bone fracture healing and improved bone grafts. Acne, alopecia, skin conditions such as dry skin (lack of dermal hydration), undue skin slackness (insufficient skin firmness), insufficient sebum secretion and wrinkles, and hypertension are other conditions which may be treated with the compound of the invention.

The above compound is also characterized by high cell differentiation activity. Thus, this compound also provides a therapeutic agent for the treatment of psoriasis, or as an anti-cancer agent, especially against leukemia, colon cancer, breast cancer and prostate cancer. The compound may be present in a composition to treat psoriasis in an amount from about 0.01 μg/gm to about 50 μg/gm of the composition, and may be administered topically, transdermally, orally or parenterally in dosages of from about 0.01 μg/day to about 10 μg/day.

It has also been discovered that this compound increases breaking strength (cortical strength) as well as crushing strength (trabecular strength) of bones. Thus, this compound could also be used in conjunction with bone replacement procedures such as hip replacements, knee replacements, and the like.

DETAILED DESCRIPTION OF THE INVENTION 2-methylene-19-nor-20(S)-1α,25-dihydroxyvitamin $D_3$ (referred to herein as 2MD) was synthesized and tested. Structurally, this 19-nor analog is characterized by the general formula I previously illustrated herein.

The preparation of 2-methylene-19-nor-20(S)-1α,25-dihydroxyvitamin $D_3$ having the basic structure I can be accomplished by a common general method, i.e. the condensation of a bicyclic Windaus-Grundmann type ketone II with the allylic phosphine oxide III to the corresponding 2-methylene-19-nor-vitamin D analog IV followed by deprotection at C-1 and C-3 in the latter compound:

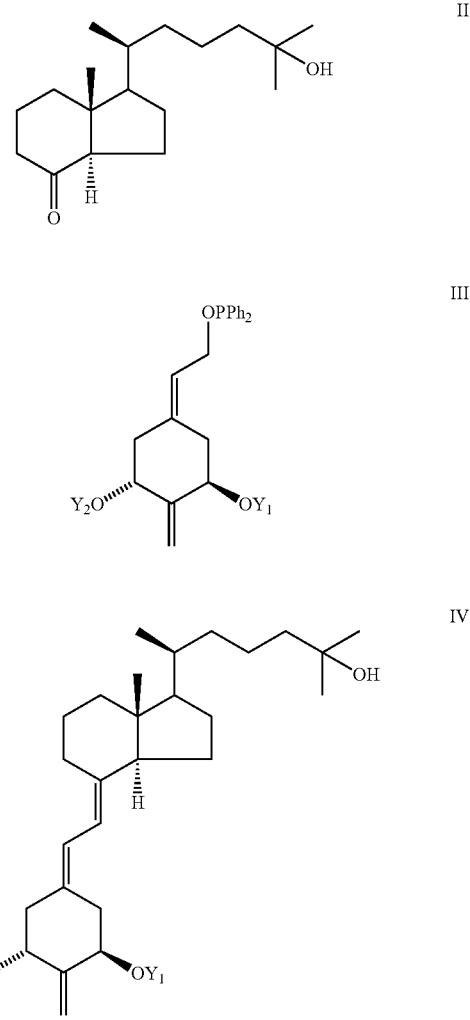

In the structures II, III, and IV groups $Y_1$ and $Y_2$ are hydroxy-protecting groups, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

Hydrindanones of the general structure II are known, or can be prepared by known methods.

For the preparation of the required phosphine oxides of general structure III, a new synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compound I is illustrated and described more completely in U.S. Pat. No. 5,843,928 issued Dec. 1, 1998 and entitled "2-Alkylidene-19-Nor-Vitamin D Compounds" the specification of which is specifically incorporated herein by reference.

Biological Activity of 2-methylene-20(S)-19-nor-1, 25-$(OH)_2D_3$

Figure 1:
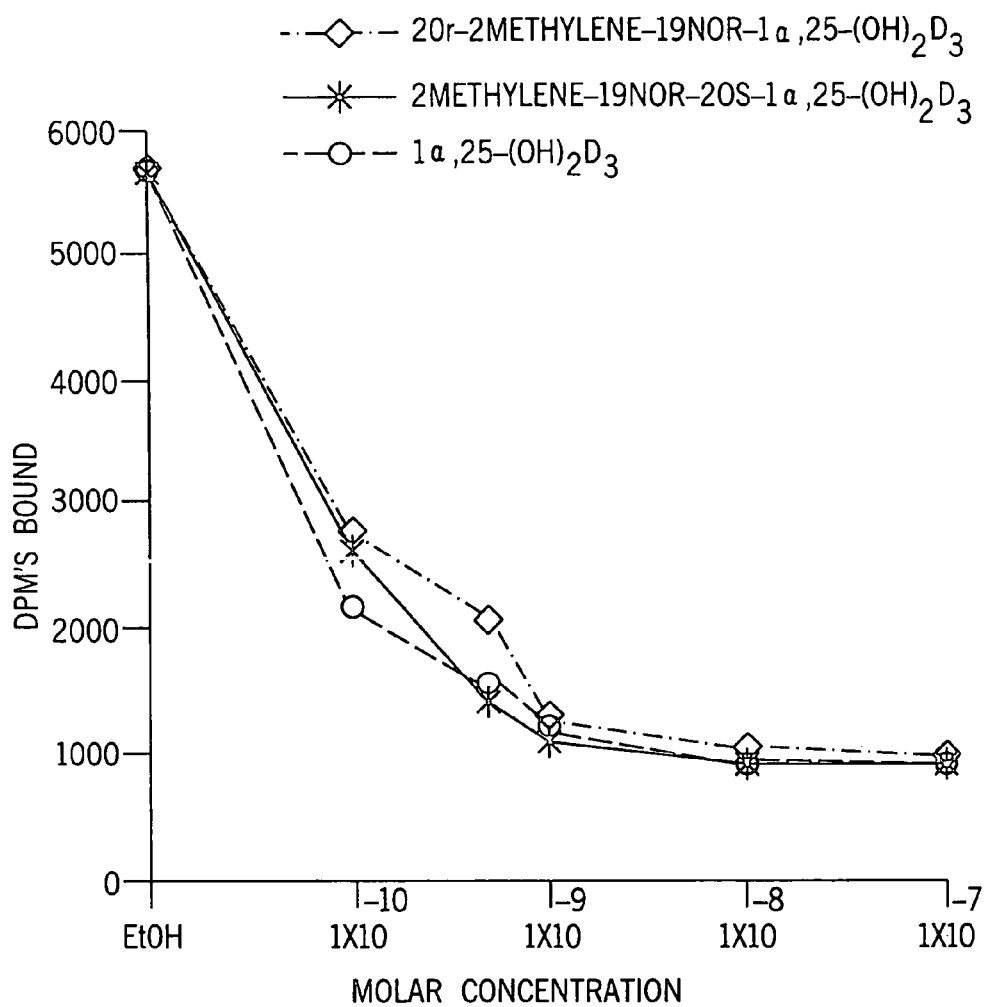
FIG. 1 is a graph illustrating the relative activity of 2-methylene-19-nor-20(S)-1α,25-dihydroxyvitamin $D_3$, 2-methylene-19-nor-1α,25-dihydroxyvitamin $D_3$ and 1α,25-dihydroxyvitamin $D_3$ to compete for binding of [3H]-1,25-$(OH)_2$-$D_3$ to the vitamin D pig intestinal nuclear receptor.

The introduction of a methylene group to the 2-position of the 20(S) isomer of 19-nor-1,25-$(OH)_2D_3$ had little or no effect on binding to the porcine intestinal vitamin D receptor. This compound bound equally well to the porcine receptor as compared to the standard 1,25-$(OH)_2D_3$ (FIG. 1). It might be expected from these results that this compound would have equivalent biological activity. Surprisingly, however, the 2 methylene and 20(S) substitutions produced a highly selective analog with its primary action on bone.

Figure 2:
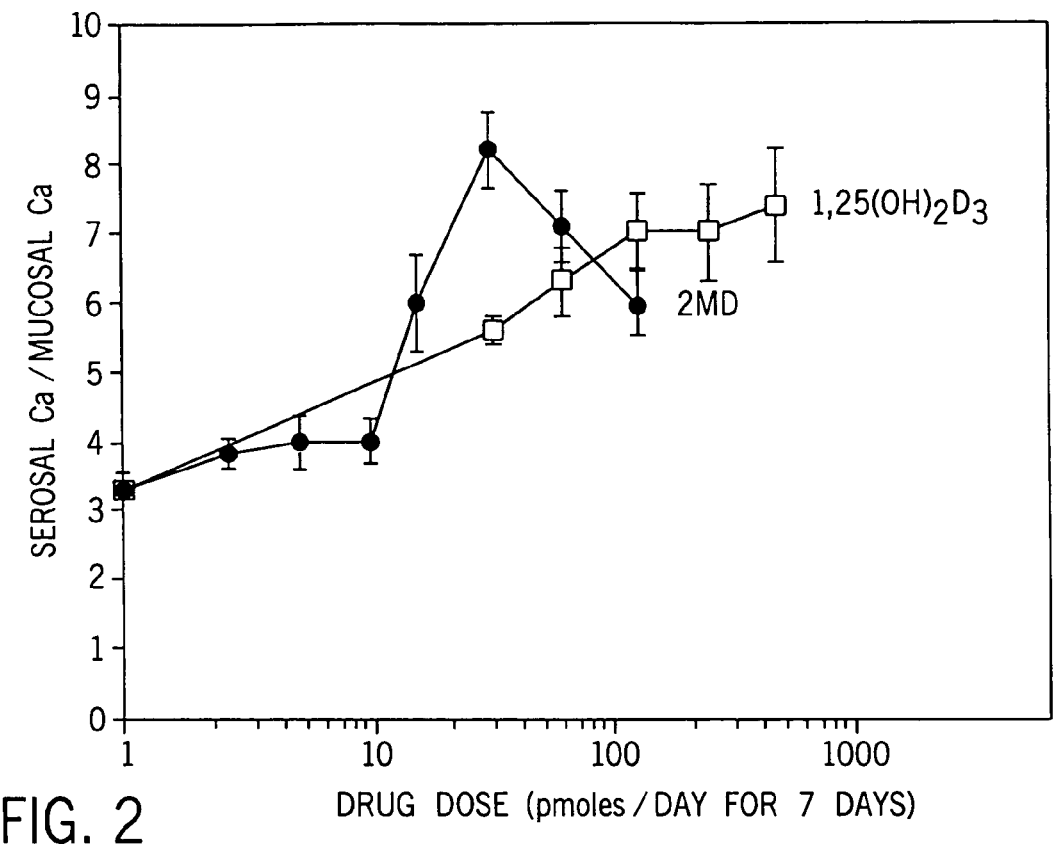
FIG. 2 is a graph illustrating the intestinal calcium transport activity of 2-methylene-19-nor-20(S)-1α,25-dihydroxyvitamin $D_3$ as compared to 1α,25-dihydroxyvitamin $D_3$.

FIG. 2 shows that 2MD has activity similar to that of 1,25-dihydroxyvitamin $D_3$ (1,25$(OH)_2D_3$), the natural hormone, in stimulating intestinal calcium transport.

Figure 3:
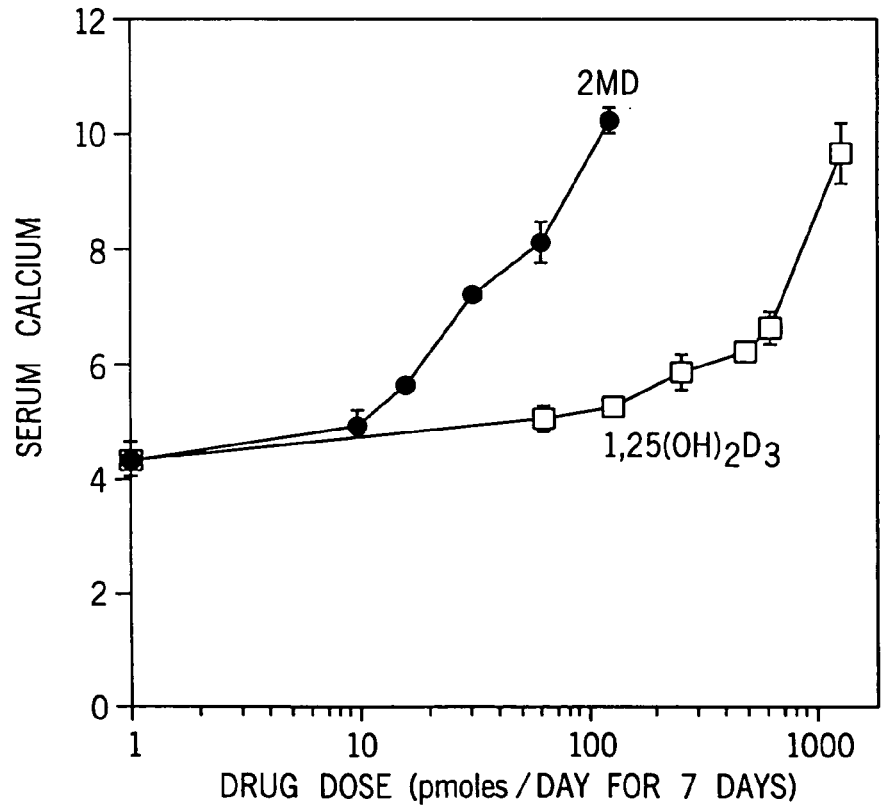
FIG. 3 is a graph illustrating the bone calcium mobilization activity of 2-methylene-19-nor-20(S)-1α,25-dihydroxyvitamin $D_3$ as compared to 1α,25-dihydroxyvitamin $D_3$.

FIG. 3 clearly demonstrates that 2MD is 100 times more potent than 1,25$(OH)_2D_3$ on bone, i.e. the mobilization of bone calcium.

Figure 4:
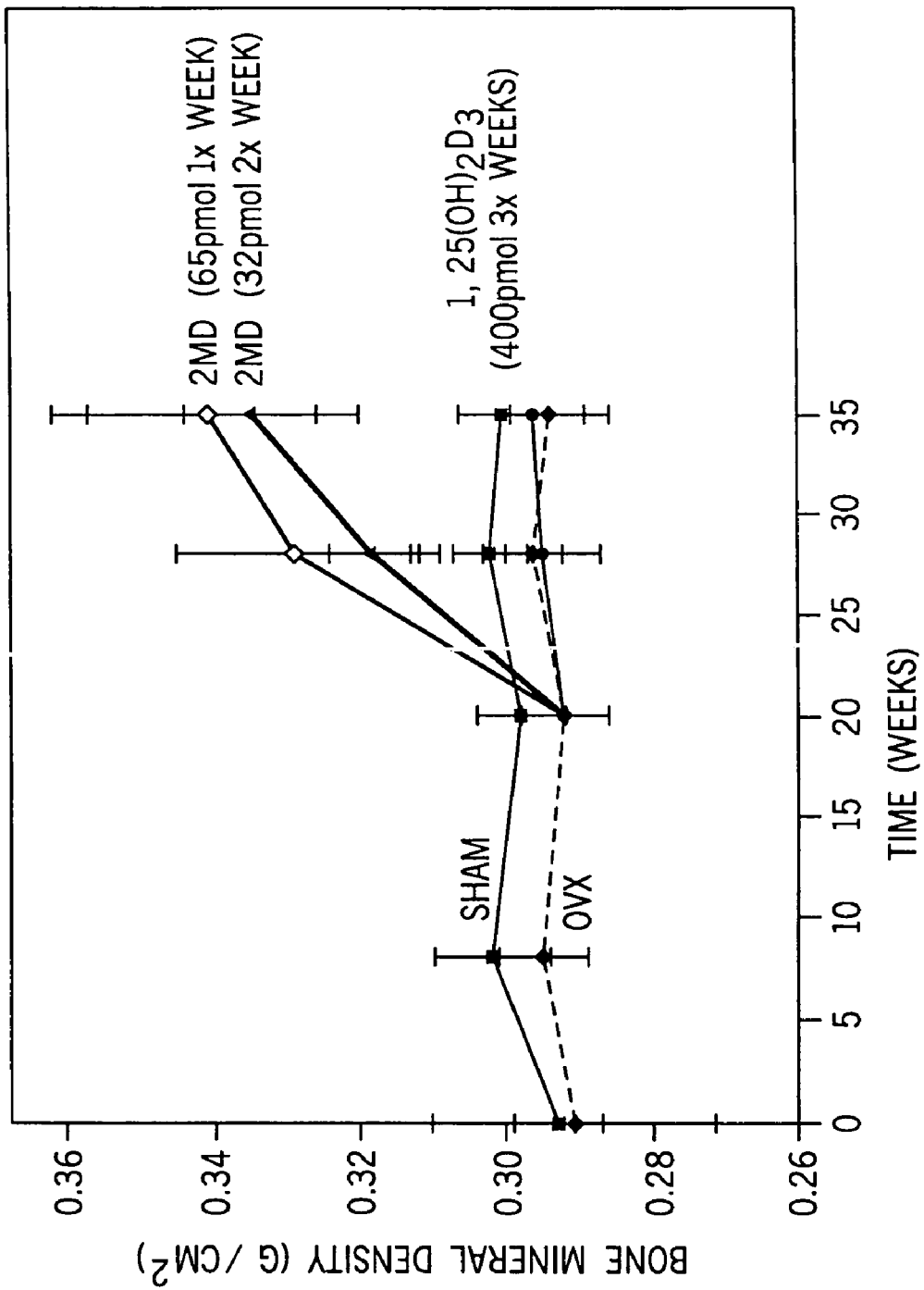
FIG. 4 is a graph illustrating the bone mineral density in ovariectomized old female rats as a result of treatment with 2-methylene-19-nor-20(S)-1α,25-dihydroxyvitamin $D_3$, as compared to 1α,25-dihydroxyvitamin $D_3$.

FIG. 4 shows that 2MD is extraordinarily effective in building bone mass in ovariectomized rats as compared to the native hormone without increasing serum calcium concentration. This is as yet an unprecedented new finding for a vitamin D compound.

Figure 5:
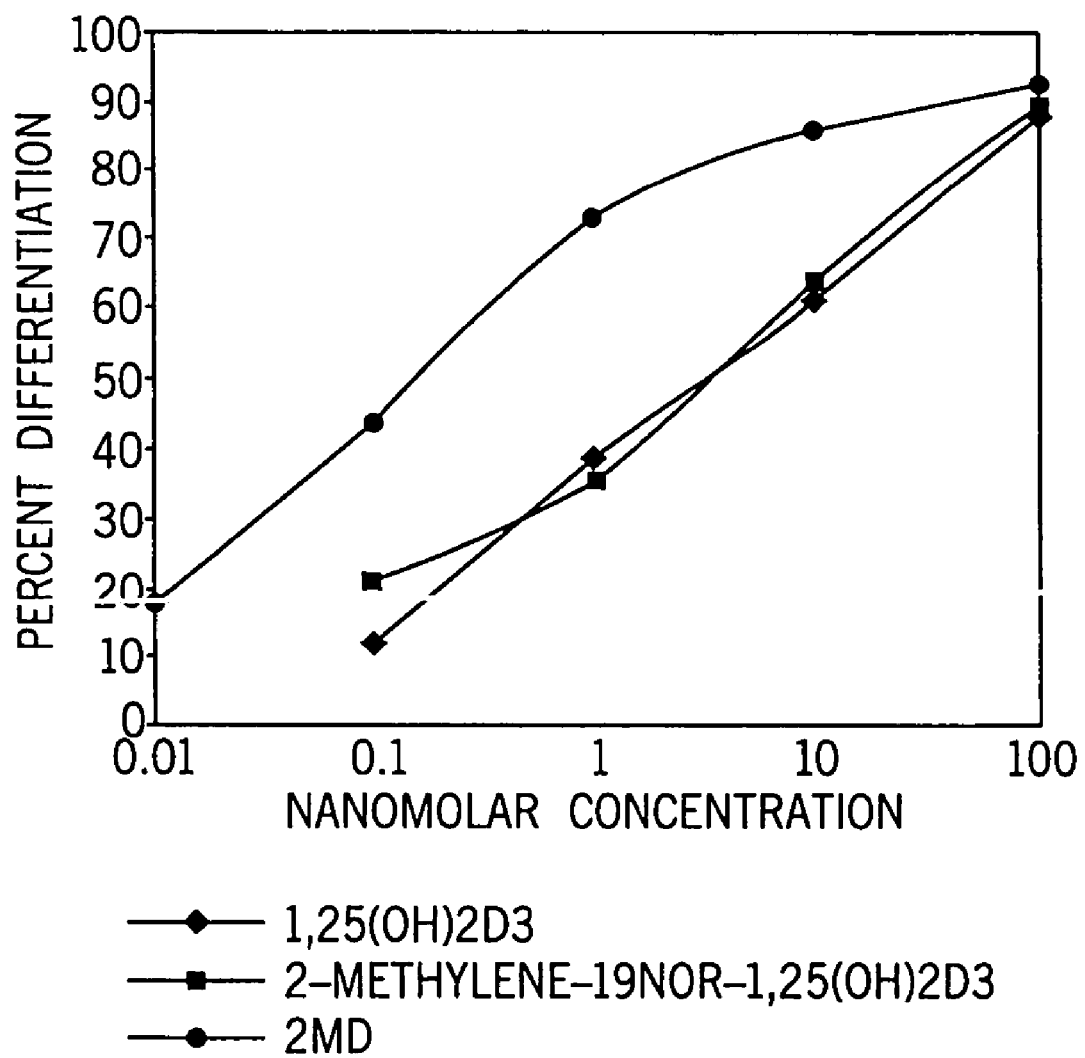
FIG. 5 is a graph illustrating the percent HL-60 cell differentiation as a function of the concentration of 2-methylene-19-nor-20(S)-1α,25-dihydroxyvitamin $D_3$, 2-methylene-19-nor-1α,25-dihydroxyvitamin $D_3$ and 1α,25-dihydroxyvitamin $D_3$.

FIG. 5 illustrates that 2MD is 50–100 times more potent than 1,25$(OH)_2D_3$ on HL-60 differentiation, making it an excellent candidate for the treatment of psoriasis and cancer, especially against leukemia, colon cancer, breast cancer and prostate cancer.

Figure 6A:
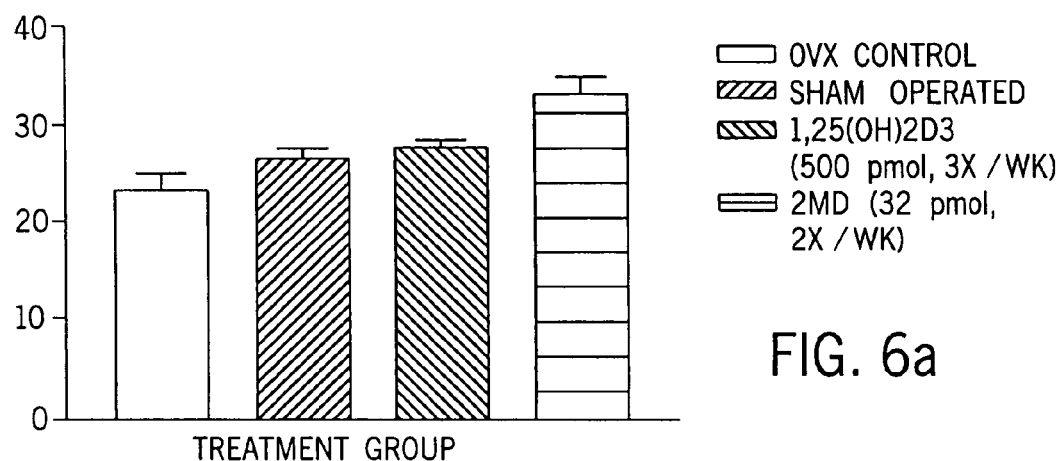
FIG. 6a is a bar graph illustrating the restoration and building of bone in ovariectomized old female rats as a result of treatment with 2-methylene-19-nor-20(S)-1α,25-dihydroxyvitamin $D_3$ as compared to 1α,25-dihydroxyvitamin $D_3$.

Table 1 and FIG. 6a illustrate that 2MD is very effective in restoring bone of ovariectomized, old female rats at 32 pmol given 2 times per week as compared to 1,25$(OH)_2D_3$ given at high doses 3 times per week. Note: 2MD also increases % ash in the femur.

Figure 6B:
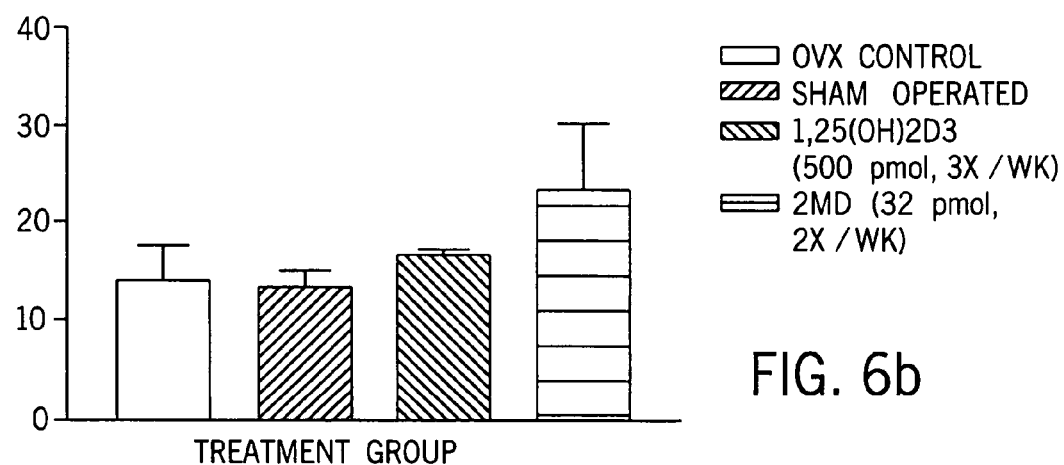
FIG. 6b is a bar graph illustrating the increase of bone strengthen ovariectomized old female rats as a result of treatment with 2-methylene-19-nor-20(S)-1α,25-dihydroxyvitamin $D_3$ as compared to 1α,25-dihydroxyvitamin $D_3$.

Table 2 and FIG. 6b show that 2MD increases breaking strength in the femurs (cortical strength) and crushing strength in the vertebra (trabecular strength) of animals shown in Table 1.

Figure 7:
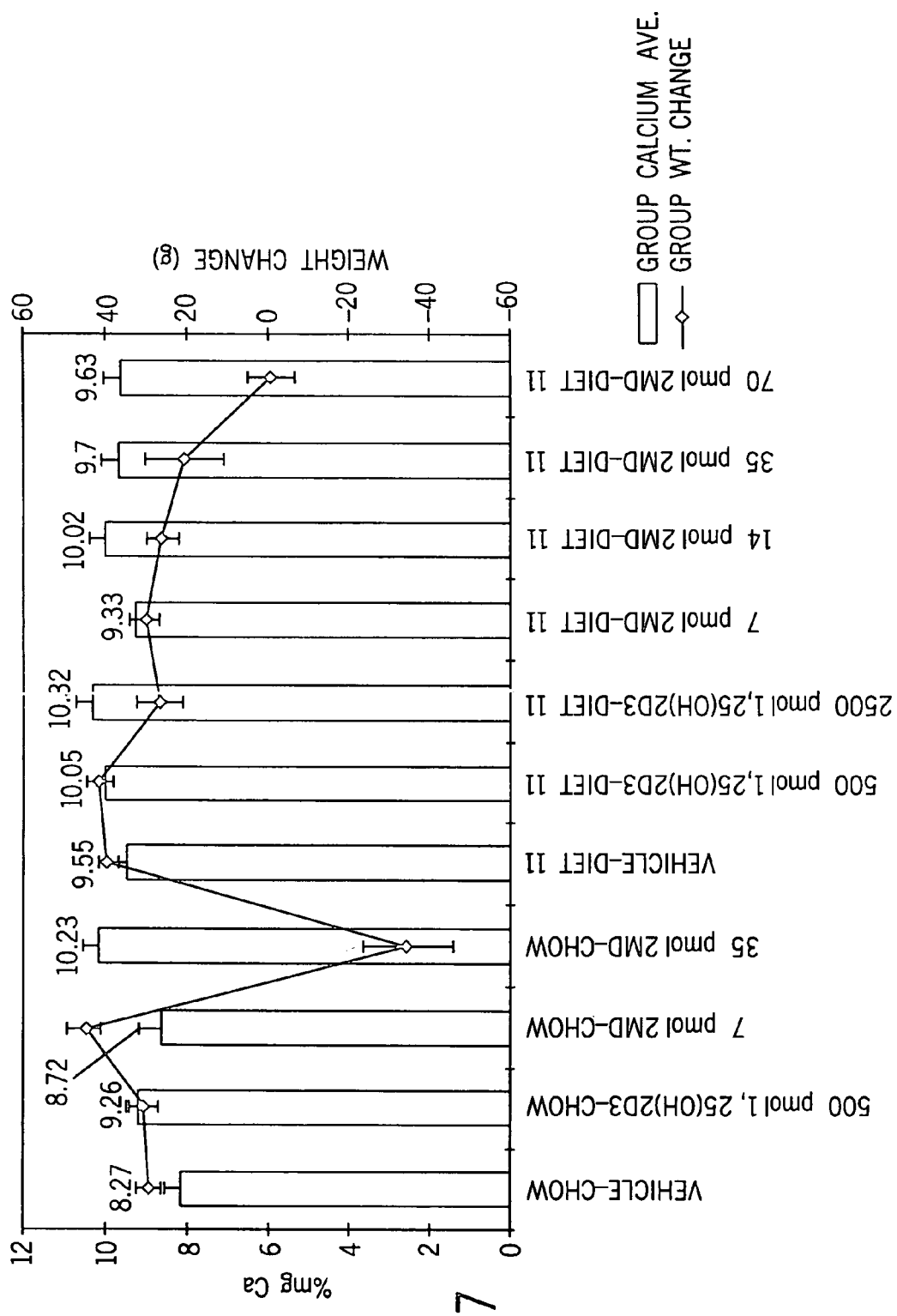
FIG. 7 is a bar graph illustrating blood serum calcium levels in ovariectomized old female rats after 6 weeks of treatment at various dosages of 2-methylene-19-nor-20(S)-1α,25-dihydroxyvitamin $D_3$ as compared to 1α,25-dihydroxyvitamin $D_3$.
Figure 8:
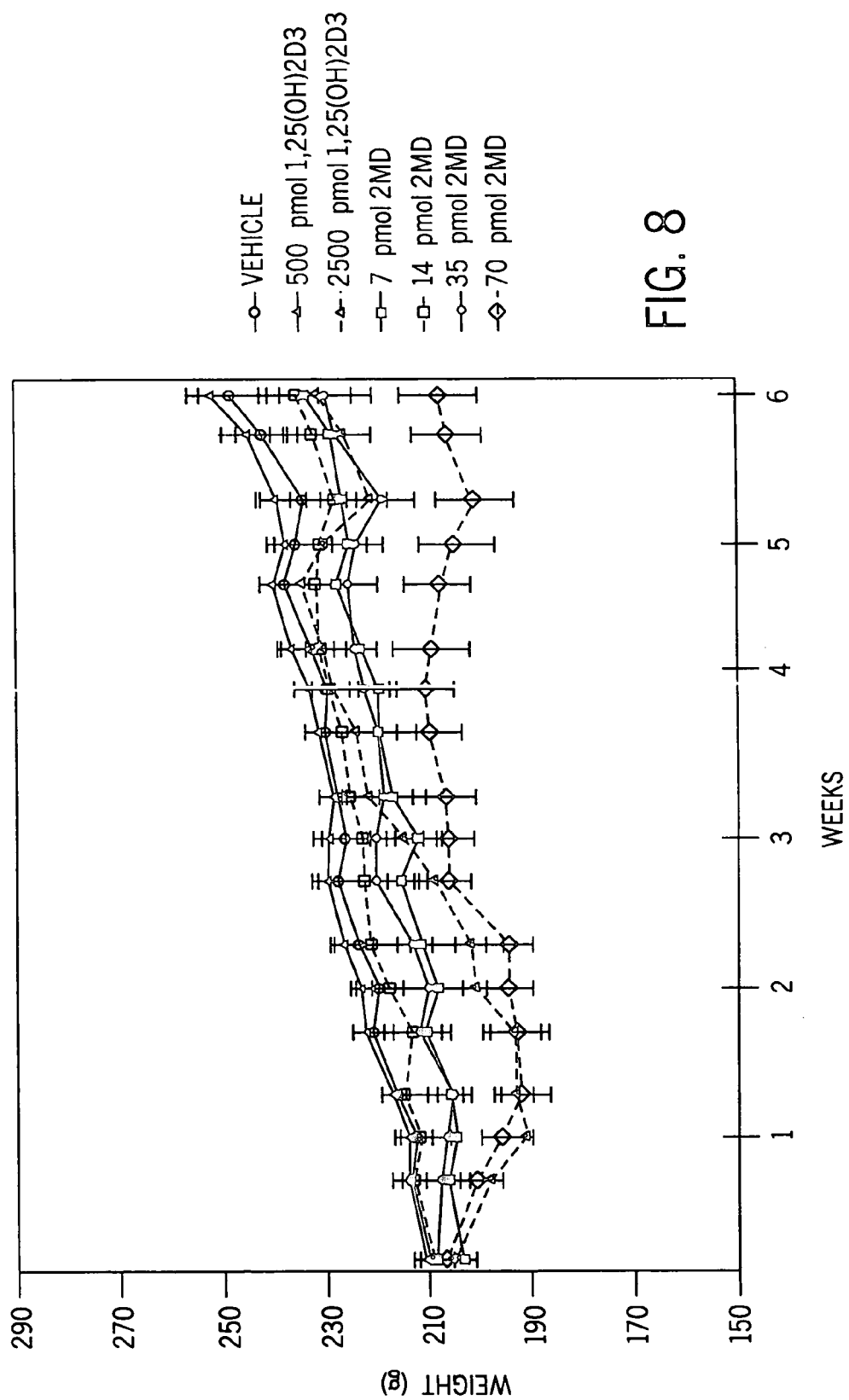
FIG. 8 is a graph illustrating the growth of ovariectomized old female rats at various dosages of 2-methylene-19-nor-20(S)-1α,25-dihydroxyvitamin $D_3$ as compared to 1α,25-dihydroxyvitamin $D_3$.

FIGS. 7 and 8 snow a six week toxicity study in rats showing that 2MD appears safe at up to 30 pmol/day. Further, in Rhesus monkeys, a single oral dose of 27 µg does not cause significant elevation of serum calcium concentration, suggesting even greater safety in primates.

Competitive binding of the analogs to the porcine intestinal receptor was carried out by the method described by Dame et al (Biochemistry 25, 4523–4534, 1986).

The differentiation of HL-60 promyelocytic into monocytes was determined as described by Ostrem et al (J. Biol. Chem. 262,14164–14171, 1987).

Interpretation of Data

The in vivo tests of increasing serum calcium of rats on a zero calcium diet provides an insight to osteoblastic or bone activity of 2MD. The dose response curves show that 2MD is at least 80 times more potent than 1,25$(OH)_2D_3$ in raising calcium in the plasma via the stimulation of the osteoblasts (FIG. 3). At the same time, the activity of 2MD on intestinal calcium transport is approximately equal that of 1,25-$(OH)_2D_3$ (FIG. 2). Therefore, these data show 2MD to have selective activity on bone.

2MD is about as active as 1,25$(OH)_2D_3$ in binding to the vitamin D receptor (FIG. 1). However, it is between 10–100 times more active than 1,25-$(OH)_2D_3$ in causing differentiation of the promyelocyte, HL-60, into the monocyte (FIG. 5). This result suggests that 2MD will be very effective in psoriasis because it has direct cellular activity in causing differentiation and in suppressing growth. It also indicates that it will have significant activity as an anti-cancer agent, especially against leukemia, colon cancer, breast cancer and prostate cancer.

The most important result, however, is that 2MD is extremely effective not only in restoring bone mass of ovariectomized, old female breeder rats as shown in FIGS. 4 and 6 and Tables 1 and 2, but it causes an increase in bone mass above that of sham-operated controls. This illustrates that 2MD is very likely having an anabolic effect on bone or increasing bone formation. Importantly, the increased bone mass provided by 2MD translates into marked increases in bone strength. This increased strength to fracture in femur shows cortical strength while increased strength to crush fractures of vertebra illustrates trabecular bone strength (Table 2 and FIGS. 6a and 6b). Interestingly, even the percent ash is unexpectedly increased further by 2MD. Of great importance is that at the dosage levels used in this study, there was no change in serum calcium of animals that showed the marked elevation of bone mass. This argues that a window of safety exists between the use of 2MD to increase bone mineral content and the action of 2MD in elevating serum calcium.

Preliminary safety tests carried out on two different occasions have revealed that female rats on a high calcium chow diet tolerate 30 pmol/day without elevating serum calcium or causing mineralization of the kidney (see FIGS. 7 and 8). Further, preliminary studies in Rhesus monkeys indicates that primates tolerate 2MD extremely well since a dose of as much as 27 µg of this compound was given as a single does to a 10 Kg Rhesus monkey without appreciably elevating serum calcium concentration. These and other tests indicate that primates will tolerate 2MD extremely well which may give a very large window between efficacy and the danger of hypercalcemia in man.

These results illustrate that 2MD is an excellent candidate for an anti-osteoporosis therapy and that it may be useful in a number of other circumstances such as autoimmune diseases, cancer, and psoriasis.

TABLE 1

Treatment of Ovariectomized Rats with 1,25-(OH)$_2$D$_3$ and 2MD

| Group | Treatment | Treatment Time (Weeks) | BMD (g/cm$^2$) | BMC (g) | Body Wt. (g) | BMC/Body Wt. (mg/g) | Serum CA (mg/dl) | Femur Ash (%) | Femur Ash (mg) |
|---|---|---|---|---|---|---|---|---|---|
| OVX Control | Oil Vehicle/ 5X/Week | 8 | 0.294 ± 0.004 | 8.64 ± 3.30 | 414 ± 15 | 21.4 ± 1.20 | — | — | — |
| | | 17 | 0.296 ± 0.003 | 9.34 ± 0.50 | 422 ± 19 | 22.3 ± 1.69 | — | — | — |
| | | 30 | 0.296 ± 0.003 | 9.41 ± 0.45 | 404 ± 24 | 23.4 ± 1.60 | 11.1 ± 0.17 | 59.2 ± 0.82 | 386 ± 21.6 |
| Sham Operated | Oil Vehicle/ 5X/Week | 8 | 0.302 ± 0.003 | 9.34 ± 0.38 | 356 ± 14 | 26.3 ± 0.76 | | | |
| | | 17 | 0.300 ± 0.002 | 9.14 ± 0.54 | 351 ± 15 | 26.4 ± 0.82 | | | |
| | | 30 | 0.297 ± 0.004 | 9.20 ± 0.53 | 340 ± 13 | 26.7 ± 1.20 | 11.8 ± 0.20 | 81.5 ± 1.20 | 400 ± 18.0 |
| 1,25(OH)$_2$D$_3$ | 250 pmol/d/ 5X/Week | 8 | 0.297 ± 0.001 | 8.90 ± 0.40 | 399 ± 9.3 | 22.4 ± 0.48 | | | |
| | | 17 | 0.308 ± 0.008 | 9.6 ± 0.39 | 394 ± 11 | 24.5 ± 0.87 | | | |
| | | 30 | 0.310 ± 0.007 | 10.1 ± 0.30 | 392 ± 16 | 26.1 ± 0.97 | 11.4 ± 0.21 | 60.8 ± 1.1 | 417 ± 23 |
| 1,25(OH)$_2$D$_3$ | 500 pmol/d/ 5X/Week | 8 | 0.312 ± 0.005 | 10.2 ± 0.40 | 397 ± 14.2 | 26.3 ± 0.57 | | | |
| | 3X/Week | 17 | 0.331 ± 0.008 | 11.5 ± 0.25 | 421 ± 12.8 | 27.6 ± 0.68 | | | |
| | 3X/Week | 30 | 0.328 ± 0.008 | 11.8 ± 0.23 | 432 ± 23.0 | 28.0 ± 0.69 | 11.9 ± 0.20 | 61.4 ± 1.3 | 478 ± 7.5 |
| 2MD | 32 pmol/d/ 2X/Week | 8 | 0.295 ± 0.009 | 8.4 ± 0.13 | 375 ± 8.2 | 22.4 ± 0.64 | | | |
| | | 17 | 0.313 ± 0.011 | 9.7 ± 0.19 | 373 ± 11.0 | 26.2 ± 0.92 | | | |
| | | 30 | 0.331 ± 0.006 | 11.6 ± 0.40 | 346 ± 11.0 | 33.4 ± 1.60 | 10.8 ± 0.22 | 65.6 ± 1.7 | 462 ± 21.4 |
| 2MD | 65 pmol/d/ 1X/Week | 8 | 0.293 ± 0.004 | 8.5 ± 0.23 | 408 ± 10.5 | 22.2 ± 0.53 | | | |
| | | 17 | 0.312 ± 0.005 | 9.6 ± 0.24 | 402 ± 11.3 | 24.0 ± 0.80 | | | |
| | | 30 | 0.310 ± 0.009 | 10.2 ± 0.33 | 393 ± 15.0 | 26.0 ± 1.10 | 10.7 ± 0.46 | 62.5 ± 0.57 | 443 ± 11.6 |

All animals were ovariectomized except the sham-operated controls. Values are expressed as mean ± SEM.

TABLE 2

Strength of Femurs and Vertebrae to Mechanical Stress

| Group | Treatment | Stress Value Femur | Stress Value Vertebra |
|---|---|---|---|
| OVX Control | Oil Vehicle/5X/Week | 109.31 ± 19.60 | 14.26 ± 3.58 |
| Sham-Operated | Oil Vehicle/5X/Week | 121.36 ± 12.5 | 13.67 ± 1.79 |
| 1,25(OH)$_2$D$_3$ | 250 pmol/day/5X/Week | 118.21 ± 19.85 | 19.24 ± 5.66 |
| 1,25(OH)$_2$D$_3$ | 500 pmol/d/3-5X/Week | 116.47 ± 16.20 | 17.14 ± 0.52 |
| 2MD | 32 pmol/d/2X/Week | 134.84 ± 14.12 | 23.93 ± 6.59 |
| 2MD | 65 pmol/d/1X/Week | 133.71 ± 14.06 | 17.07 ± 5.73 |

For treatment purposes, the compound of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compound may be administered orally, topically, parenterally or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.1 µg to 10 µg per day of the compounds are appropriate for treatment purposes, such doses being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin D$_2$ or D$_3$, or 1α,25-dihydroxyvitamin D$_3$—in situations where different degrees of bone mineral mobilization and calcium transport stimulation is found to be advantageous.

Compositions for use in the above-mentioned treatment of psoriasis and other malignancies comprise an effective amount of the 2-methylene-20(S)-19-nor-vitamin D compound as defined by the above formula I as the active ingredient, and a suitable carrier. An effective amount of such compound for use in accordance with this invention is from about 0.01 µg to about 50 µg per gm of composition, and may be administered topically, transdermally, orally or parenterally in dosages of from about 0.1 µg/day to about 1 µg/day.

The compound may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compound is advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizers or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A method of treating leukemia comprising administering to a patient with said leukemia an effective amount of 2-methylene-19-nor-20(S)-1α,25-dihydroxyvitamin $D_3$ having the formula:

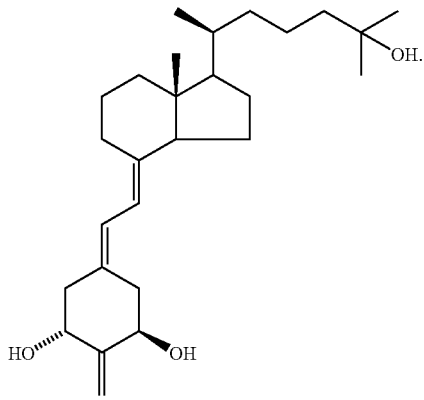

2. The method of claim 1 wherein 2-methylene-19-nor-20(S)-1α,25-dihydroxyvitamin $D_3$ is administered orally.

3. The method of claim 1 wherein 2-methylene-19-nor-20(S)-1α,25-dihydroxyvitamin $D_3$ is administered parenterally.

4. The method of claim 1 wherein 2-methylene-19-nor-20(S)-1α,25-dihydroxyvitamin $D_3$ is administered transdermally.

5. The method of claim 1 wherein 2-methylene-19-nor-20(S)-1α,25-dihydroxyvitamin $D_3$ is administered in a dosage of from about 0.01 μg/day to about 10 μg/day.

6. A method of treating colon cancer, breast cancer or prostate cancer comprising administering to a patient with said disease an effective amount of 2-methylene-19-nor-20(S)-1α,25-dihydroxyvitamin $D_3$ having the formula:

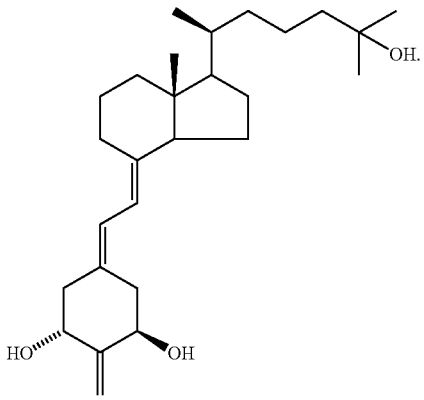

7. The method of claim 6 wherein 2-methylene-1 9-nor-20(S)- 1α,25-dihydroxyvitamin $D_3$ is administered orally.

8. The method of claim 6 wherein 2-methylene-19-nor-20(S)-1α,25-dihydroxyvitamin $D_3$ is administered parenterally.

9. The method of claim 6 wherein 2-methylene-19-nor-20(S)-1α,25-dihydroxyvitamin $D_3$ is administered transdermally.

10. The method of claim 6 wherein 2-methylene-19-nor-20(S)-1α,25-dihydroxyvitamin $D_3$ is administered in a dosage of from about 0.01 μg/day to about 10 μg/day.

* * * * *